United States Patent [19]

Downs et al.

[11] Patent Number: 4,798,841

[45] Date of Patent: Jan. 17, 1989

[54] TETRAHYDROPYRIDINE OXIME CHOLINERGIC AGENTS AND METHOD OF TREATMENT

[75] Inventors: David A. Downs; Walter H. Moos; David W. Moreland; Haile Tecle, all of Ann Arbor, Mich.

[73] Assignee: Warner-Lambert Company, Morris Plains, N.J.

[21] Appl. No.: 32,839

[22] Filed: Mar. 31, 1987

[51] Int. Cl.$^4$ ..................... A61K 31/44; C07D 213/04
[52] U.S. Cl. ..................................... 514/357; 546/338
[58] Field of Search ....................... 546/338; 514/357

[56] References Cited

U.S. PATENT DOCUMENTS 3,004,979 10/1961 Druey et al. ..................... 546/338

FOREIGN PATENT DOCUMENTS 51-1638 1/1976 Japan ................................. 371/221

Primary Examiner—Mary C. Lee
Assistant Examiner—Zinna Northington
Attorney, Agent, or Firm—Ronald A. Daignault

[57] ABSTRACT

Certain N-substituted 1-(1,2,3,6-tetrahydro-3-pyridinyl)oximes and N-substituted 1-(1,2,3,6-tetrahydro-4-pyridinyl)oximes are useful as analgesic agents or agents for the teatment or amelioration of the symptoms of cerebral insufficiency characterized by decreased central acetylcholine production or release.

12 Claims, No Drawings

TETRAHYDROPYRIDINE OXIME CHOLINERGIC AGENTS AND METHOD OF TREATMENT

BACKGROUND OF THE INVENTION

The present invention relates to chemical compounds, pharmaceutical compositions, and to a method of treatment employing the compounds and compositions. More particularly, the present invention is concerned with certain 1,2,5,6-tetrahydro-1-substituted 3- or 4-pyridine oximes, to pharmaceutical compositions containing these compounds, and to a pharmaceutical method of treatment.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced by as much as ninety percent. (See Davies et al., *The Lancet*, 1976 (Vol. 2): 1403; Perry et al., *J. Neurol. Sci.*, 34: 247–265 (1977); and White et al., *The Lancet*, 1977 (Volume 1): 668–670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e. are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging*, 4: 25–30 (1983)). Aged humans and non-human primates with decreased cognition show improved memory when they are treated, for example, with acetylcholinesterase inhibitors such as physostigmine. These agents increase the available supply of synaptic acetylcholine by inhibiting its hydrolysis.

Aminopyridines such as 3,4-diaminopyridine ameliorate age-related cognitive deficits by increasing the release of acetylcholine from presynaptic nerve terminals, thus increasing synaptic acetylcholine. (See H. P. Davis et al., *Exp. Aging Res.*, 9: 211–214 (1983)).

It has been known for some time that the natural alkaloid, muscarine, has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Arecoline (the methyl ester of 1,2,5,6-tetra-hydro-1-methyl-3-pyridinecarboxylic acid) is the chief alkaloid found in betel nuts (*Areca catechu*). Betel nuts have been chewed by natives of the East Indies since early times as a euphoretic. The present pharmaceutical utility of arecoline, however, has been limited to its use as a veterinary anthelmintic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double blind study. (See Christie et al., *Brit. J. Psychiatry*, 138: 46–50 (1981)).

Certain 3- or 4-ketoximes of 1-(lower alkyl)-1,2,5,6-tetrahydropyridines in which the oxygen is unsubstituted are disclosed in U.S. Pat. No. 3,004,979, having utility as parasympathomimetic agents acting on non-striated muscle.

Regarding analgesia, the literature indicates that acetylcholine and muscarine agonists possess antinociceptive activity (see T. T. Chau et al., *J. Pharmacol. Exp. Ther.*, 222: 612–666 (1982),; W. L. Dewey et al., *Life Sci.*, 17: 9–10 (1975); and N. W. Pedigo et al., *Neurosci. Lett.*, 26: 85–90 (1981) and references cited therein).

SUMMARY OF THE INVENTION

The present invention provides a method of treating the symptoms of cognitive decline in the elderly comprising the administration of an effective amount of a compound of formula 1:

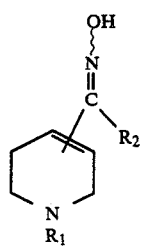

wherein the

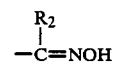

may be attached to the tetrahydropyridine moiety at either carbon atom number 3 or 4 of the tetrahydropyridine ring system, and the attachment of the OH group to the nitrogen atom is configured either syn- or anti- to the tetrahydropyridine ring.

The substituent group $R_1$ is hydrogen; straight or branched alkyl of from one to six carbon atoms optionally substituted with hydroxy or alkoxyl of from one to four carbon atoms; straight or branched alkenyl of from one to six carbon atoms optionally substituted with hydroxy or alkoxyl of from one to four carbon atoms; straight or branched alkynyl of from one to six carbon atoms optionally substituted with hydroxy or alkoxyl of from one to four carbon atoms; cycloalkyl of from three to eight carbon atoms;

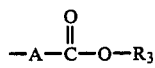

where A is a bond or is a hydrocarbon chain of from one to four carbon atoms and when containing two or more carbon atoms may contain one double bond and where $R_3$ is alkyl of from one to six carbon atoms, optionally substituted with halogen;

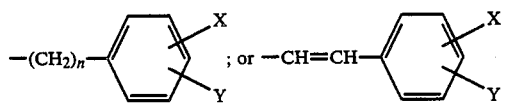

where n is zero to four and X and Y are independently selected from hydrogen, fluorine, chlorine, bromine, hydroxy, straight or branched alkyl of from one to three carbon atoms, or alkoxyl of from one to four carbon atoms.

$R_2$ is selected from hydrogen; straight or branched alkyl of from one to six carbon atoms optionally substituted with hydroxy or alkoxyl of from one to four carbon atoms; straight or branched alkenyl of from one to six carbon atoms optionally substituted with hydroxy or alkoxyl of from one to four carbon atoms; straight or branched alkynyl of from one to six carbon atoms optionally substituted with hydroxy or alkoxyl of from one to four carbon atoms; cycloalkyl of from three to six carbon atoms; or

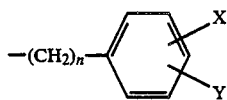

where n is zero, two, three or four and X and Y are independently selected from hydrogen, fluorine, chlorine, bromine, hydroxy, straight or branched alkyl of from one to three carbon atoms, or alkoxyl of from one to four carbon atoms; alkylcarbonyl of from two to twelve carbon atoms; alkenylcarbonyl of from three to twelve carbon atoms; alkynylcarbonyl of from three to twelve carbon atoms; or a pharmaceutically acceptable acid addition salt thereof.

In another aspect, the present invention provides a method of treating pain in a mammal in need of such treatment comprising the administration of an analgesically effective amount of a compound of formula 1 above in combination with a pharmaceutically acceptable carrier.

In another aspect, the present invention provides pharmaceutical compositions for treating the symptoms of cognitive decline in the elderly comprising administering an effective amount of a compound of formula 1 above in combination with a pharmaceutically acceptable carrier.

In yet another aspect, the present invention provides pharmaceutical compositions useful as analgesic agents comprising an analgesically effective amount of a compound as defined above in combination with a pharmaceutically acceptable carrier.

DETAILED DESCRIPTION

The compounds of the present invention comprise a class of 1,2,5,6-tetrahydro-1 substituted 3- or 4-pyridine oximes and their pharmaceutically acceptable salts which are centrally acting muscarinic agents and which are thus useful as analgesic agents, sleep aids, or therapeutic agents for treating cholinergic deficit states such as senile dementia, Alzheimer's disease, Huntington's chorea, tardive dyskinesia, hyperkinesia, mania or similar conditions of cerebral insufficiency characterized by decreased cerebral acetylcholine production or release.

The substituent group $R_1$ in structural formula 1 above is selected from hydrogen; straight or branched alkyl of from one to six carbon atoms optionally substituted with hydroxy or alkoxyl of from one to four carbon atoms; straight or branched alkenyl of from one to six carbon atoms optionally substituted with hydroxy or alkoxyl of from one to four carbon atoms; straight or branched alkynyl of from one to six carbon atoms optionally substituted with hydroxy or alkoxyl of from one to four carbon atoms; cycloalkyl of from three to eight carbon atoms;

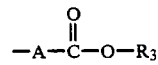

where A is a bond or a hydrocarbon chain of from zero to four carbon atoms and when containing two or more carbon atoms may contain one double bond and $R_3$ is alkyl of from one to six carbon atoms, optionally substituted with halogen; or

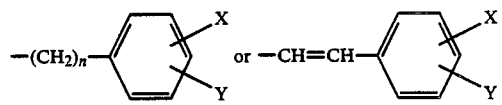

where n is zero to four and X and Y are independently selected from hydrogen, fluorine, chlorine, bromine, hydroxy, straight or branched alkyl of from one to three carbon atoms, or alkoxyl of from one to four carbon atoms.

The term "alkyl of from one to six carbon atoms" denotes a substituent group derived from a saturated hydrocarbon by removal of a single hydrogen atom. The term includes methyl, ethyl, n-propyl, iso-propyl, n-butyl, sec-butyl, iso-butyl, tert-butyl, and the various isomeric forms of pentyl and hexyl. Likewise, the terms "alkenyl of from one to six carbon atoms" and "alkynyl of from one to six carbon atoms" denote substituent groups derived, respectively, from alkene or alkyne hydrocarbons by the removal of a single hydrogen atom. These terms include ethenyl, ethynyl, propenyl, propynyl, and similar branched and unbranched unsaturated hydrocarbon groups of up to six carbon atoms.

The term "cycloalkyl of from three to eight carbon atoms" denotes saturated carbocyclic rings such as cyclopropyl, cyclobutyl, cyclopentyl, cyclohexyl, as well as alkyl substituted carbocyclic rings containing up to eight carbon atoms such as methyl-, dimethyl-, and ethylcyclohexyl.

The term "alkoxyl" denotes a substitent group derived by removal of the hydrogen from the oxygen atom of a saturated alcohol and attached to the parent molecular moiety through the oxygen atom. Such groups include methoxyl, ethoxyl, 1- and 2-propoxyl, and similar branched and unbranched alkoxyl groups of up to four carbon atoms.

The terms "alkylcarbonyl," "alkenylcarbonyl," and "alkynylcarbonyl" denote susbstituent alkyl, alkenyl, or alkynyl groups as previously defined, attached to the parent molecular moiety through a carbonyl group.

In compounds of the present invention, the substituent group $R_2$ is selected from hydrogen; straight or branched alkyl of from one to six carbon atoms optionally substituted with hydroxy or alkoxyl of from one to four carbon atoms; straight or branched alkenyl of from one to six carbon atoms optionally substituted with hydroxy or alkoxyl of from one to four carbon atoms; straight or branched alkynyl of from one to six carbon atoms optionally substituted with hydroxy or alkoxyl of from one to four carbon atoms; cycloalkyl of from three to six carbon atoms; or

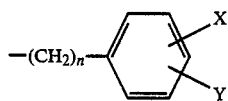

where n is zero to four and X and Y are independently selected from hydrogen, fluorine, chlorine, bromine, hydroxy, straight or branched alkyl of from one to three carbon atoms, or alkoxyl of from one to four carbon atoms; alkylcarbonyl of from two to twelve carbon atoms; alkenylcarbonyl of from three to twelve carbon atoms; or alkynylcarbonyl of from three to twelve carbon atoms.

Preferred compounds for use in the pharmaceutical methods of the present invention are those in which $R_1$ and $R_2$ are alkyl.

The compounds employed in the method of this invention may exist in either of two isomeric forms in which the hydrogen atom of the oxime group may be either syn- or anti- with respect to the tetrahydropyridine ring. The present invention includes both forms of the compounds as well as mixtures of the syn- and anti-forms. Moreover, in those compounds in which there is a double bond in a carbon chain, both the Z (i.e. cis-) and E (i.e. trans) forms are included in the present invention. The terms syn- and anti- as they apply to the compounds of the present invention are illustrated by formulas 1a and 1b:

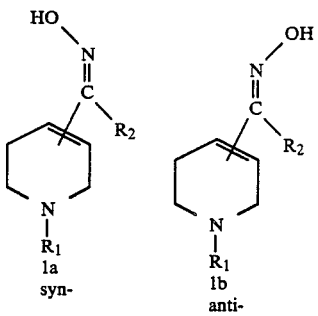

Examples of compounds contemplated as falling within the scope of the present invention include, but are not limited to the following:

1-(1,2,5,6-Tetrahydro-1-methyl-3-pyridinyl)-1-pentanone oxime.

1-(1,2,5,6-Tetrahydro-1-methyl-3-pyridinyl)-1-propanone oxime.

1-(1,2,5,6-Tetrahydro-1-methyl-3-pyridinyl)-ethanone oxime.

1,2,5,6-Tetrahydro-1-methyl-3-pyridine-carboxaldehyde oxime.

2-Methyl-1-(1,2,5,6-tetrahydro-1-methyl-3-pyridinyl)-1-propanone oxime.

1-(1,2,5,6-Tetrahydro-1-methyl-3-pyridinyl)-4-penten-1-one oxime.

4-Methoxy-1-(1,2,5,6-tetrahydro-1-methyl-3-pyridinyl)-1-butanone oxime.

3-Phenyl-1-(1,2,5,6-tetrahydro-1-methyl-3-pyridinyl)-1-propanone oxime.

1-[1,2,5,6-Tetrahydro-1-(1-methylethyl)-3-pyridinyl]ethanone oxime.

1-(1-Ethyl-1,2,5,6-tetrahydro-3-pyridinyl)-ethanone oxime.

1-(1,2,5,6-Tetrahydro-1-methyl-3-pyridinyl)-3-butyn-1-one oxime.

1-[1,2,5,6-Tetrahydro-1-(2-propenyl)-3pyridinyl]ethanone oxime.

Phenyl(1,2,5,6-tetrahydro-1-methyl-3-pyridinyl)methanone oxime.

1-[1-Cyclopentyl-1,2,5,6-tetrahydro-3-pyridinyl]ethanone oxime.

3-Phenyl-1-(1,2,5,6-tetrahydro-1-propyl-3-pyridinyl)-1-propanone oxime.

1-(1,2,5,6-Tetrahydro-3-pyridinyl)ethanone oxime.

1-(1,2,5,6-Tetrahydro-1-methyl-3-pyridinyl)-4-hexyn-1-one oxime.

1-(1,2,3,6-Tetrahydro-4-pyridinyl)ethanone oxime.

Compounds of the present invention are prepared by the general synthetic method detailed in Reaction Sequence 1, following.

Referring to the Reaction Sequence, the starting 3- or 4-ketopyridines, 5, are prepared by one of three alternative methods. In the first method, the known 3- or 4-pyridinecarbonitriles, 2, are reacted in the conventional manner with the desired alkyl lithium compound or the appropriate Grignard reagent in an aprotic solvent such as diethyl ether, tetrahydrofuran, dioxane or the like, followed by hydrolysis in dilute aqueous acid. In the second method, the known 3- or 4-pyridinecarbonyl chlorides, 3, are reacted in the usual manner with the desired alkyl lithium compound in the presence of a copper(I) halide.

Reaction Sequence 1
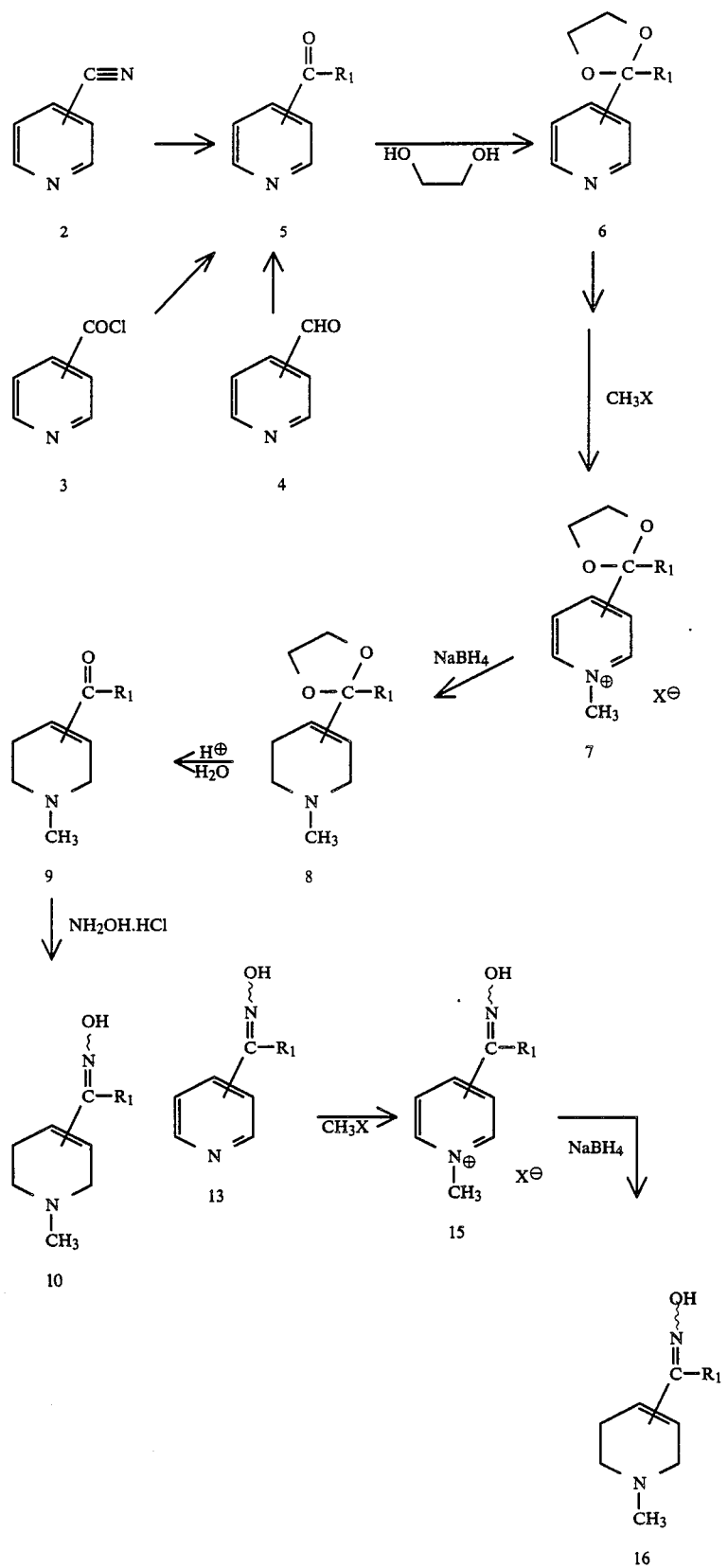
In the third alternative method, the known 3- or 4-pyridine- carboxaldehydes, 4, from which the aldoximes The 3- or 4-ketopyridines, 5 thus produced, are reacted with a diol such as ethanediol in the presence of acid to produce the 3- or 4-pyridine-ketals, 6. The ketals, 6, are converted by the action of the desired alkyl, alkenyl, alkynyl, or aralkyl halide (preferably the iodide) to the corresponding N-substitutedpyridinium ketals, 7. The N-substitutedpyridinium ketals, 7, are subsequently reduced by the action of an alkali metal hydride, such as sodium borohydride, to produce the N-substituted 3- or 4-ethylene-dioxyketal-1,2,5,6-tetrahydropyridines, 8.

The 3- or 4-ethylenedioxyketal-1,2,5,6-tetrahydropyridines, 8, are next converted to the corresponding N-substituted 3- or 4-keto-1,2,5,6-tetrahydropyridines, 9, by the action of aqueous acid. The 3- or 4-keto-1,2,5,6-tetrahydropyridines, 9, are then reacted with hydroxylamine hydrochloride in, for example, methanol under reflux for a period sufficient to effect the formation of the corresponding oximes, 10.

Alternatively, the unsubstituted oximes, 13, are converted to the corresponding N-substituted pyridinium iodides by reaction with the desired iodide. These pyridinium salts are reduced by the action of sodium borohydride, generally in a mixed water/alcohol medium at ambient temperature, to produce the N-substituted 3- or 4-oximino-1,2,5,6-tetrahydropyridine compounds of the present invention.

By virtue of the basic nitrogen atom in the tetrahydropyridine ring, the compounds of the present invention form pharmaceutically acceptable acid addition salts with organic and inorganic acids. Examples of suitable acids for the formation of pharmaceutically acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane- and ethanesulfonic, hydroxymethane- and hydroxyethanesulfonic, and the like. (See for example, "Pharmaceutical Salts," J. Pharm. Sci. 66 (1): 1–19 (1977)).

In a similar manner, the N-lower-alkyl and lower-dialkyl tetrahydropyridinium salts may be used in the method of this invention as, for example the N-methyl-, N,N-dimethyl- and N-ethyl-1,2,5,6-tetrahydro- pyridinium halides.

The acid addition salts are prepared by contacting the free base form of the compounds of this invention with a sufficient amount of the desired acid to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

The free acid or base forms of the compounds of this invention differ somewhat from their respective salt forms in such physical properties as melting point and solubility in polar solvents, but the salts are otherwise equivalent to their respective free acid or base forms for the purposes of the invention.

The compounds of the present invention are centrally acting muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

The compounds of the present invention may also be co-administered when desired with anticholinergic agents, for example, atropine, methylatropine, glycopyrrolate, scopolamine, methylscopolamine, propantheline, pirenzepine, and AF-DX-116, to reduce cholinergic side effects.

The biological activity of compounds of the present invention was evaluated using a number of tests. The activity of compounds of this invention as central muscarinic binding site agonists and antagonists was measured. In the RQNB screening assay, which is described more fully by Mark Watson, et al, J. Pharmacol. and Exp. Ther., 237 (2): 411 (1986), rat cerebral cortex tissue was treated with radio-labeled quinuclidinyl benzilate, a known muscarinic binding site antagonist. The percent inhibition at a given concentration or concentrations of test compound required to inhibit 50% of the binding of this muscarinic antagonist were then determined.

Similarly, in the RCMD screening assay, described more fully by T. W. Vickeroy et al., J. Pharmacol. and Exp. Ther., 229 (3): 747 (1984), rat cerebral cortex tissue was treated with radiolabeled cis-methyldioxolane, a known muscarinic binding site agonist. The percent inhibition at given concentrations or concentrations of test compounds required to inhibit 50% of the binding of this muscarinic agonist were then determined. These values are reported as $IC_{50}$ concentrations in Table 1 and demonstrate that the compounds of the present invention possess significant muscarinic activity.

A second screening assay, designated PIT, determined the activity of representative compounds of the present invention as muscarinic agonists. In this assay, rat cortex slices bearing muscarinic binding sites were incubated with the test compound. The production of inositol phosphates was then measured. Stimulation of phosphatidyl inositol turnover reflects the degree of muscarinic agonist activity of the tested compound. The values indicating percent stimulation of phosphatidyl inositol turnover, relative to carbachol, (PIT) appear in Table 2.

In the scopolamine induced swimming test (SIS), the ability of representative compounds of the present invention to reverse the hyperactive swimming behavior of laboratory rats given scopolamine was assessed. In this test, untreated rats will generally swim between 20 to 30 meters during a five minute test period. Rats given scopolamine at does of 0.1 mg/kg develop a stereotypical swimming hyperactivity with the swimming distances generally increasing by 75–125% above baseline values. This increase in swimming hyperactivity can be reversed by administration of physostigmine or the cholinergic agonist, arecoline. The effect of scopolamine is centrally mediated; the ability of a test compound to reverse the hyperactive swimming behavior induced by scopolamine is thus a measure of the central cholinergic activity of the compound.

TABLE 1

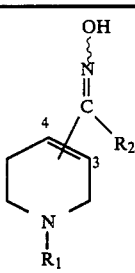

| $R_1$ | $R_2$ | $IC_{50}$ (Nanomolar) RQNB | RCMD |
|---|---|---|---|
| Hydrogen | 3-Methyl | 24% Inhib. @ $10^{-6}$ M | 85% Inhib. @ $10^{-7}$ M |
| n-Propyl | 3-Phenylmethyl | 63% Inhib. @ $10^{-6}$ M | 3% Inhib. @ $10^{-7}$ M |
| Methyl | 3-n-Butyl | 300 | 20 |
| Methyl | 3-Ethyl | 2000 | 50 |
| Methyl | 3-Methyl | 4650 | 19 |
| Methyl | Hydrogen | 8% Inhib. @ $10^{-6}$ M | 22% Inhib. @ $10^{-7}$ M |
| Methyl | 3-(1-Methylethyl) (syn) | 35% Inhib. @ $10^{-6}$ M | 43% Inhib. @ $10^{-7}$ M |
| Methyl | 3-(1-Methylethyl) (anti) | 10% Inhib. @ $10^{-6}$ M | 10% Inhib. @ $10^{-7}$ M |
| Methyl | 3-($-CH_2CH_2CH=CH_2$) | 600 | 40 |
| Methyl | 3-($-CH_2CH_2CH_2OCH_3$) | 2500 | 30 |
| Methyl | 3-Phenylmethyl | 86% Inhib. @ $10^{-6}$ M | 66% Inhib. @ $10^{-7}$ M |
| Methyl | 4-Methyl | 10,000 | 490 |
| Ethyl | 3-Methyl | 23% Inhib. @ $10^{-6}$ M | 21% Inhib. @ $10^{-7}$ M |
| Methyl | 3-($-CH_2CH_2C\ CH$) | 1000 | 7 |
| Methyl | 3-($-CH_2OCH_2Ph$) | 38% Inhib. @ $10^{-6}$ M | 30% Inhib. @ $10^{-7}$ M |
| Methyl | 3-Phenyl | 51% Inhib. @ $10^{-6}$ M | 39% Inhib. @ $10^{-7}$ M |

TABLE 2

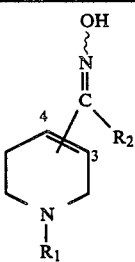

| $R_1$ | $R_2$ | Percent Stimulation of Phosphatidyl Inositol Turnover (PIT) at $10^{-3}$ M |
|---|---|---|
| Methyl | 3-($-CH_2CH_2CH=CH_2$) | 21 |
| Methyl | 3-Methyl | 16 |
| Methyl | 3-n-Butyl | 15 |
| Methyl | 3-Ethyl | 15 |

The minimal effect dose (MED) for several representative compounds of this invention required to demonstrate reversal of the scopolamine-induced hyperactive swimming activity in laboratory rats is presented in Table 3.

TABLE 3

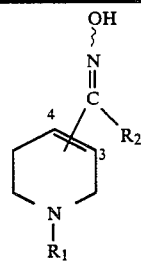

| | | Minimal Effective Dose (mg/kg) for Reversal of Scopolamine-Induced Swimming Hyperactivity | |
|---|---|---|---|
| $R_1$ | $R_2$ | (Subcutaneous) | (Oral) |
| Methyl | 3-Ethyl | 32 | — |
| Methyl | 3-n-Butyl | 32 | — |
| Methyl | 3-Methyl | 3.2 | — |
| Methyl | 3-Hydrogen | 32 | — |
| Methyl | 3-($-CH_2CH_2CH=CH_2$) | 32 | — |
| Methyl | 3-($-CH_2CH_2CH_2OCH_3$) | 32 | — |
| Methyl | 3-($-CH_2CH_2-Ph$) | 32 | — |
| Methyl | 4-Methyl | 3.2 | — |
| n-Propyl | 3-($-CH_2CH_2-Ph$) | — | 3.2 |
| Hydrogen | 3-Methyl | 3.2 | |

The antiwrithing (AW) test provides preliminary assessment of compounds with potential analgesic activity. The test is performed with male Swiss-Webster mice. Compounds are administered in aqueous 0.2% methylcellulose or other appropriate vehicles in volumes of 10 ml/kg. Dosages represent active moiety.

Acetic acid (0.6%, 10 ml/kg) is injected intraperitoneally after administration of the compound. writhing movements are counted for five minutes starting seven minutes after the acetic acid injection. Data are expressed as $ED_{50}$ values, where the $ED_{50}$ is the dose necessary to suppress writhing by 50% relative to vehicle controls. $ED_{50}$ values are calculated by nonlinear regression analysis.

In the antiwrithing analgesia test, compound of the present invention, 1-(1,2,5,6-tetrahydro-1-methyl-3-pyridinyl)ethanone oxime, demonstrated an $ED_{50}$ value of 1.1 mg/kg upon intraperitoneal dosing.

In therapeutic use as agents for treating pain or for treating cerebral insufficiency, the compounds utilized in the pharmaceutical method of this invention are administered to the patient at dosage levels of from 0.7 to 7000 mg per day. For a normal human adult of approximately 70 kg of body weight, this translates into a dosage of from 0.01 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the phrmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of the present invention may also be co-administered when desired with anticholinergic agents, for example, atropine, methylatropine, glycopyrrolate, scopolamine, methylscopolamine, pirenzepine, and AF-DX-116, to reduce cholinergic side effects.

The following preparative examples are provided to enable one skilled in the art to practice the invention. They are illustrative of the present invention and are not to be read as limiting the scope of the invention as it is defined by the appended claims.

Examples of General Synthetic Methods and Preparation of Starting Materials

EXAMPLE 1

Representative Example of the Conversion of a Pyridine Carboxaldehyde to a Ketopyridine—Preparation of 1-(3-Pyridinyl)propanone 3-Pyridinecarboxaldehyde (10.71 g, 100 mmol) was dissolved in 200 ml of tetrahydrofuran under a nitrogen atmosphere and cooled to $-30°$ C. Ethylmagnesium bromide (100 mmol, 2.0 molar in tetrahydrofuran) was slowly added, after which the mixture was stirred at $-30°$ C. for one hour. Saturated ammonium chloride solution was added and the mixture was allowed to warm to room temperature. Diethyl ether (200 ml) was added and the organic layer was separated, dried over anhydrous magnesium sulfate, and evaporated to yield the intermediate carbinol as a yellow oil. This material was taken up in 500 ml of toluene, and 26.1 g (300 mmol) of manganese dioxide was added. The resulting mixture was heated under reflux for two hours under a nitrogen atmosphere in a flask fitted with a Dean Stark trap to collect water which was azeotropically removed.

The reaction mixture was cooled to room temperature and diluted by the addition of diethyl ether. The reaction mixture is filtered and the solvents were removed from the filtrate under vacuum and the crude product purified by chromatography on a silica gel column, eluting with 1:1 hexane/ethyl acetate to produce 7.09 g of 1-(3-pyridinyl)-1-propanone.

EXAMPLE 2

Representative Example of the Conversion of a Pyridinecarbonyl Chloride to a Ketopyridine—Preparation of 1-(3-Pyridinyl)pentanone Copper(I) iodide (3.8 g, 2.0 mmol) was suspended in 30 ml of dry tetrahydrofuran which was then cooled to $-40°$ C. n-Butyl lithium solution (16 ml, 2.5 molar in tetrahydrofuran) was added and the mixture further cooled to $-78°$ C. and stirred for one hour. 3-Pyridinecarbonyl chloride hydrochloride (1.78 g, 10 mmol) was quickly added, and the resulting mixture was allowed to slowly warm to room temperature. The reaction was quenched by the addition of 2 ml of methanol, and the mixture partitioned between diethyl ether and 1:1 saturated aqueous ammonium chloride/aqueous ammonia.

This mixture was stirred until the aqueous layer became dark blue (copper ammonia complex), after which the layers were separated. The organic layer was washed successively with portions of 10% aqeuous $Na_2S_2O_3$, water, and brine, and then dried over anhydrous magnesium sulfate. The solvent was removed under vacuum and the crude product chromatographed on silica gel, eluting with 70% hexane in ethyl acetate, to yield 0.80 g of 1-(3-pyridinyl)-1-pentanone.

EXAMPLE 3

Representative Example of the Preparation of a Ketopyridine by the Swern Oxidation of an Intermediate Carbinol Prepared via Grignard Reaction—Preparation of 2-Methyl-1-(3-pyridinyl)-1-propanone Oxalyl chloride was distilled under a nitrogen atmosphere immediately prior to use; 10.93 g (86.13 mmol) was dissolved in 200 ml of dichloromethane. This mixture was cooled, under a nitrogen atmosphere, to −50° C. and 13.45 g (12.22 ml, 172.3 mmol) of dry dimethylsulfoxide in 50 ml of dichloromethane were slowly added. The resulting mixture was stirred at −50° C. for ten minutes. α-(1-Methylethyl)-3-pyridine-methanol (11.84 g, 78.3 mmol, previously prepared by reaction of 3-pyridinecarboxaldehyde with isopropylmagnesium bromide) in 50 ml of dichloromethane was added. This mixture was stirred at −50° C. for one hour, after which time 39.6 g (54.57 ml, 391.5 mmol) of triethylamine were added. This mixture was allowed to slowly warm to room temperature.

Water (300 ml) was added to the mixture, and the layers were separated. The water layer was extracted twice with dichloromethane, and the organic solutions were combined, washed with successive portions of 10% aqueous sodium carbonate solution, and brine, and then dried over anhydrous magnesium sulfate. The solvents were removed under vacuum, and the crude product was chromatographed over silica gel, eluting with 15% ethyl acetate in chloroform to yield 10.3 g of 2-methyl-1(3-pyridinyl)-1-propanone.

EXAMPLE 4

Representative Example of the Conversion of a Ketopyridine to a Keto-1,2,5,6-tetrahydropyridine—Preparation of 1-(1,2,5,6-Tetrahydro-1-methyl-3-pyridinyl)-1-pentanone 1-(3-Pyridinyl)-1-pentanone (4.53 g, 27.75 mmol, prepared as described in Example 2 above), 1,2-ethanediol (2.58 g, 2.32 ml, 41.63 mmol), and p-toluenesulfonic acid (6.3 g, 33.3 mmol) were dissolved in 50 ml of toluene at room temperature. This mixture was heated under reflux for twenty hours in a flask fitted with a Dean Stark trap to collect azeotropically distilled water.

After this time, the mixture was cooled and poured into 10% aqueous sodium carbonate solution and the resulting mixture diluted with diethyl ether. The organic layer was separated, dried over anhydrous magnesium sulfate, and evaportaed to yield the crude ethylene ketal as an orange oil. The crude product was purified by chromatography over silica gel, eluting with 70% hexane in ethyl acetate to produce 4.22 g of the pure material.

The ethylene ketal was mixed with 10 ml of methyl iodide and stirred at room temperature for three days. The excess methyl iodide was removed under vacuum, and the residue triturated with diethyl ether to obtain 6.78 g of the N-methylpyridinium ethylene ketal iodide.

The N-methylpyridinium ethylene ketal iodide was dissolved in 60 ml of absolute ethanol under nitrogen, and 0.81 g of sodium borohydride were slowly added, keeping the temperature of the reaction mixture under 25° C. This was followed by addition of another 1.32 g of sodium borohydride. This mixture was stirred at room temperature for 30 minutes, after which time the mixture was heated under reflux for thirty minutes.

The reaction mixture was cooled to room temperature and 21 ml of 6M aqueous hydrochloric acid were slowly added. After addition of the acid was complete, the resulting mixture was heated under reflux for one hour and then cooled to room temperature. The alcohol was removed under vacuum leaving a yellowish slurry. Fifty ml of water were added, followed by the slow addition of 20 g of potassium carbonate. The resulting mixture was extracted twice with diethyl ether and the extract was dried over anhydrous magnesium sulfate. The ether was evaporated and the residue was purified by column chromatography over silica gel, eluting with 5% methanol in diethyl ether, to yield 2 g of 1-(1,2,5,6-tetrahydro-1-methyl-3-pyridinyl)-1-pentanone as a yellow oil. This material was reacted with oxalic acid to yield 1.3 g of the ethanedioate salt, mp 171°-172° C.

EXAMPLE 5

Representative Example of the Preparation of a 1,2,5,6-Tetrahydropyridine Oxime by the Oximination of a Keto-1,2,5,6-tetrahydropyridine—Preparation of 1-(1,2,5,6-tetrahydro-1-methyl-3-pyridinyl)-1-pentanone oxime To a solution of 1.09 g (6.01 mmol) of 1-(1,2,5,6-tetrahydro-1-methyl-3-pyridinyl)-1-pentanone (prepared as described in Example 4 above) in 6 ml of methanol were added 0.42 g (6.1 mmol) of hydroxylamine hydrochloride. The resulting mixture was heated under reflux for 12 hours, cooled, and stirred at room temperature for three days. The solvent was removed under vacuum and chloroform and dilute aqueous ammonium hydroxide solution were added. The chloroform layer was separated, washed with water until it tested neutral, and dried over anhydrous magnesium sulfate. The chloroform was removed under vacuum and the residual dark oil was taken up in diethyl ether. This solution was filtered through silica gel and the ether removed under vacuum. The residue was reacted with oxalic acid to produce 1-(1,2,5,6-tetrahydro-1-methyl-3-pyridinyl)-1-pentanone oxime, ethanedioate salt, mp 91°-95° C.

EXAMPLE 6

Representative Example of the Conversion of a Ketopyridine to a 1-Methyl-ketoxime-1,2,5,6-tetrahydropyridine via the Ketopyridine Oxime—Preparation of 1-(1,2,5,6-tetrahydro-1-methylpyridinyl)ethanone oxime Step 1—Preparation of 1-(3-pyridinyl)ethanone oxime A mixture of 50 g (0.41 mol) of 1-(3-pyridinyl)-ethanone and 29 g (0.42 mol) of hydroxylamine hydrochloride in 250 ml of methanol was heated under reflux for five hours. Upon cooling to room temperature, a white solid separated from the reaction mixture. This material was collected by filtration and the filtrate was concentrated to yield additional white solid. The combined solids were dissolved in water and the solution was made weakly basic by the addition of sodium bicarbonate solution while cooling. The white precipitate which formed was separated by filtration to yield 55.4 g of 1-(3-pyridinyl)ethanone oxime, mp 115°-117° C.

Step 2—Preparation of 1-(3-pyridinyl)ethanone oxime methiodide 1-(3-pyridinyl)ethanone oxime (8.8 g, 0.073 mol) was dissolved in 500 ml of acetonitrile and 10 ml (0.16 mol) of methyl iodide were added. The resulting mixture was heated under reflux for 4 hours and then cooled to room temperature. The white precipitate was collected by filtration to yield 16.45 g of 1-(3pyridinyl)ethanone oxime methiodide, mp 219°-220° C.

Step 3—Preparation of 1-(1,2,5,6-tetrahydro-1-methylpyridinyl)ethanone oxime

To a suspension of 5 g of sodium borohydride in 100 ml of 50:50 water/methanol was added, in a dropwise manner, 50 ml of a solution of 19.5 g (0.07 mol) of 1-(3-pyridinyl)ethanone oxime methiodide dissolved in 50 ml of 50:50 water/methanol while maintaining the temperature between −5° C. and 0° C.

The mixture was then allowed to warm to room temperature and was diluted with 200 ml of water. This mixture was stirred for a few minutes and the light yellow precipitate which formed was collected by filtration to yield 7.83 g of 1-(1,2,5,6-tetrahydro-1-methylpyridinyl)ethanone oxime, mp 154°–157° C.

Preparative Examples for Compounds of the Present Invention

EXAMPLE 7

Preparation of 3-Phenyl-1-(1,2,5,6-tetrahydro-1-methyl-3-pyridinyl)propanone Oxime Step 1—Preparation of 3-phenyl-1-(3-pyridinyl)-1-propanone Employing the general method of Example 1 above, 21.42 g (0.225 mol) of pyridine-3-carboxaldehyde and 27.3 ml (0.200 mol) of 2-phenylethyl bromide were converted by Grignard reaction to 40 g (94%) of (2-phenyl-3-pyridinyl)methanol and then oxidized by the action of manganese dioxide to yield a mixture of 3-phenyl-1-(3-pyridinyl)-1-propanone and 3-phenyl-1-(3-pyridinyl)-2-propen-1-one. This mixture was reduced by hydrogen over Raney nickel to produce 17.1 g of 3-phenyl-1-(3-pyridinyl)-1-propanone.

Step 2—Preparation of 3-phenyl-1-(1,2,5,6-tetrahydro-1-methyl-3-pyridinyl)-1-propanone oxime Employing the general methods of Examples 4 and 6 above, 10 g (47.3 mmol) of 3-phenyl-1-(3-pyridinyl)-1-propanone were first converted by the action of methyl iodide to the N-methylpyridinium iodide and then reduced by the action of sodium borohydride to produce 3-phenyl-1-(1,2,5,6-tetrahydro-1-methyl-3-pyridinyl)-1-propanone which was isolated as the hydrochloride salt (5.2 g, 58%), mp 195°–197° C. cl EXAMPLE 8
Preparation of 1-(1,2,5,6-Tetrahydro-1-methyl-3-pyridinyl)-3-butyne-1-one Oxime Step 1—Preparation of 4-trimethylsilyl-3-butyne-1-ol A solution of 2 mol of ethyl magnesium bromide (2.0 molar solution in tetrahydrofuran) is cooled in an ice bath and a solution of 50.5 g of 3-butyn-1-ol (0.72 mol) in 50 ml of tetrahydrofuran is slowly added. After addition is complete, the mixture was allowed to warm to room temperature and was stirred overnight. The mixture was then cooled in an ice bath and 254 ml (2 mol) of chlorotrimethylsilane was slowly added. This mixture was heated under reflux for two hours and then cooled to 20° C. and 800 ml of 1.4M aqueous sulfuric acid were added. The mixture was extracted with diethyl ether and the ether solution was dried and concentrated under vacuum. The residue was distilled to yield 72.8 g of 4-trimethylsilyl-3-butyne-1-ol, bp 43°–48° C. at 1 mm Hg.

Step 2—Preparation of 4-Bromo-1-trimethylsilyl-1butyne

4-Trimethylsilyl-3-butyne-1-ol (14.2 g, 0.1 mol) and 0.2 ml of pyridine were dissolved in 50 ml of diethyl ether under a nitrogen atmosphere. Phosphorus tribromide (3.8 ml, 0.04 mol) was slowly added and the mixture was heated under reflux for 2 hours. Isolation of the product by conventional means yielded 9.6 g of 4-bromo-1-trimethylsilyl-1-butyne as a clear liquid, bp 35°–38° C. at 1 mm Hg.

Step 3—Preparation of (4-trimethylsilylbutyn-3-yl-3-pyridinyl)methanol

Employing the general method of Example 1 above, 10.7 g (0.1 mol) of pyridine-3-carboxaldehyde and 20.5 g (0.1 mol) of 4-bromo-1-trimethylsilyl-1-butyne were converted by Grignard reaction to 5.9 g (25%) of (4-trimethylsilylbutyn-3-yl-3-pyridinyl)methanol which was employed without further purification.

Step 4—Preparation of (3-butynyl-3-pyridinyl)methanol

Four ml of a 1.0M solution of tetrabutylammonium fluoride in tetrahydrofuran was added to 0.75 g (3.21 mmol) of (4-trimethylsilylbutyn-3-yl-3-pyridinyl)-methanol in 3 ml of tetrahydrofuran and the resulting mixture was stirred at room temperature for 30 minutes. Isolation of the product yielded 0.12 g of (3-butynyl-3-pyridinyl)methanol as a brown oil.

Step 5—Preparation of 1-(3-pyridinyl)-3-butyn-1-one

Employing the Swern oxidation method of Example 3 above, 4.8 g (29.9 mmol) of (3-butynyl-3-pyridinyl)-methanol was oxidized to 2.95 g (62%) of 1-(3-pyridinyl)-3-butyn-1-one.

Step 6—Preparation of 1-(3-pyridinyl)-3-butyne-1-one oxime

Employing the general method of Example 5 above, 2.95 g (18.5 mmol) of 1-(3-pyridinyl)-3-butyne-1-one was converted to 2.1 g (66%) of the corresponding oxime by reaction with hydroxylamine hydrochloride.

Step 7—Preparation of 1-(1,2,5,6-tetrahydro-1-methyl-3-pyridinyl)-3-butyne-1-one oxime Employing the general method of Example 6 above, 2.12 g (12.2 mmol) of 1-(3-pyridinyl)-3-butyne-1-one oxime were converted to the corresponding 1-methyl pyridinium iodide and subsequently reduced by the action of sodium borohydride to produce 1.2 g of 1-(1,2,5,6-tetrahydro-1-methyl-3-pyridinyl)-3-butyne-1-one oxime which was isolated as the ethanedioate salt, mp 55°–57° C.

EXAMPLE 9

Preparation of 4-Methoxy-1-(1,2,5,6-tetrahydro-1-methyl-3-pyridinyl)-1-butanone Oxime Step 1—Preparation of 4-Chloro-1-methoxybutane 4-Chloropropanol (47.3 g, 0.5 mol) and 62.2 ml (1 mol) of methyl iodide were dissolved in 300 ml of tetrahydrofuran and the resulting solution was cooled in an ice bath. A suspension of 40 g (1 mol) of sodium hydride in oil was slowly added. When addition was complete, the reaction mixture was allowed to warm to room temperature and was stirred overnight.

The mixture was again cooled in an ice bath and 150 ml of water were added to quench the reaction. The organic layer was separated, dried over anhydrous magnesium sulfate, and the solvent evaporated under vacuum. The residue was distilled to yield 27.6 g of 4-chloro-1-methoxybutane, bp 111°–113° C.

Step 2—Preparation of 3-(Methoxypropyl)-3-pyridinylmethanol methanol

Following the general method of Example 1, 21.7 g (0.2 mol) of 4-chloro-1-methoxypropane and 21.4 g ().2 mol) of pyridine-3-carboxaldehyde were converted to 18.87 g (52%) of (4-methoxypropyl-3-pyridinyl)methanol.

Step 3—Preparation of 4-methoxy-1-(1-methyl-3-pyridinyl)butanone

Employing the Swern oxidation method of Example 3, 25.67 g (0.142 mol) of (4-methoxypropyl-3-pyridinyl)methanol were converted to 17.6 g (69%) of 4-methoxy- 1-(1-methyl-3-pyridinyl)butanone as a yellow oil which was used without further purification.

Step 4—Preparation of 4-methoxy-1-(1-methyl-3pyridinyl)butanone oxime

Employing the general method of Example 5, 8.96 g (50 mmol) of 1-(1-methyl-3-pyridinyl)butanone was converted to the corresponding oxime by reaction with 3.82 g (55 mmol) of hydroxylamine hydrochloride. The product (9.5 g, 98%) was isolated as a thick reddish oil which was used without further purification.

Step 5—Preparation of 1-(1,2,5,6-tetrahydro-1-methyl-3-pyridinyl)-4-methoxybutanone oxime Employing the general method of Example 6 above, 9.5 g (49 mmol) of 4-methoxy-1-(1-methyl-3-pyridinyl)-butanone oxime were first converted to 16.5 g of the N-methyl pyridinium iodide salt and then reduced to 1-(1,2,5,6-tetrahydro-1-methyl-3-pyridinyl)-4-methoxybutanone oxime by the action of sodium borohydride.

The title compound was isolated as the ethanedioate salt, mp 114°–116° C.

Employing the methods detailed above, the following additional compounds were prepared:

TABLE 4

| Example | Compound Name | M.P. |
|---|---|---|
| 10 | 1,2,5,6-Tetrahydro-1-methyl-3-pyridinecarboxaldehyde oxime (Isolated as the monohydrochloride) | 249–251° C. |
| 11 | 2-Methyl-1-(1,2,5,6-tetrahydro-1-methyl-3-pyridinyl)-1-propanone oxime (Isolated as the ethanedioate) | 98–102° C. |
| 12 | 1-(1,2,5,6-Tetrahydro-1-methyl-3-pyridinyl)-4-penten-1-one oxime (Isolated as the monohydrochloride) | 70–75° C. |
| 13 | 3-Phenyl-1-(1,2,5,6-tetrahydro-1-methyl-3-pyridinyl)-1-propanone oxime (Isolated as the monohydrochloride) | 195–197° C. |
| 14 | 1-[1,2,5,6-Tetrahydro-1-(1-methylethyl)-3-pyridinyl]ethanone oxime | 110–111° C. |
| 15 | 1-(1-Ethyl-1,2,5,6-tetrahydro-3-pyridinyl)ethanone oxime (Isolated as the monohydrochloride) | >250° C. |
| 16 | 1-[1,2,5,6-Tetrahydro-1-(2-propenyl)-3-pyridinyl]ethanone oxime | 102–104° C. |
| 17 | Phenyl(1,2,5,6-tetrahydro-1-methyl-3-pyridinyl)methanone oxime (Isolated as the monohydrochloride) | 225–228° C. |
| 18 | 1-[1-Cyclopentyl-1,2,5,6-tetrahydro-3-pyridinyl]ethanone oxime (Isolated as the monohydrochloride) | 268–270° C. |
| 19 | 3-Phenyl-1-(1,2,5,6-tetrahydro-1-propyl-3-pyridinyl)-1-propanone oxime (Isolated as the monohydrochloride) | 200–210° C. (Dec.) |
| 20 | 1-(1,2,5,6-Tetrahydro-3-pyridinyl)ethanone oxime (Isolated as the hydrochloride) | 227–228° C. (Dec.) |
| 21 | 1-(1,2,5,6-Tetrahydro-1-methyl-3-pyridinyl)-4-hexyn-1-one oxime (Isolated as the monohydrochloride) | 177–178° C. |
| 22 | 1-(1,2,3,6-Tetrahydro-4-pyridinyl)-ethanone oxime | 165–166° C. |

We claim:

1. A method of treating the symptoms of cognitive decline in the elderly comprising administering a cholinergically effective amount of a compound having the formula

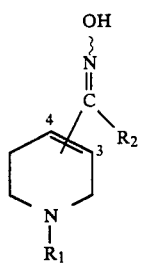

wherein
$R_1$ is hydrogen;
straight or branched alkyl of from one to six carbon atoms unsubstituted or substituted with hydroxy or alkoxyl of from one to four carbon atoms;
straight or branched alkenyl of from one to six carbon atoms unsubstituted or substituted with hydroxy or alkoxyl of from one to four carbon atoms;
straight or branched alkynyl of from one to six carbon atoms unsubstituted or substituted with hydroxy or alkoxyl of from one to four carbon atoms;
cycloalkyl of from three to eight carbon atoms;

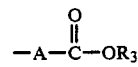

where A is a bond or is a hydrocarbon chain of from one to four carbon atoms, unsubstituted or substituted with halogen, and when containing two or more carbon atoms may contain one double bond and $R_3$ is alkyl of from one to six carbon atoms; or

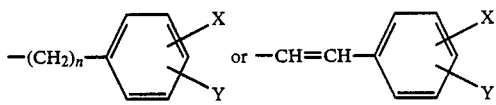

where n is zero to four and X and Y are independently selected from
hydrogen,
fluorine,
chlorine,
bromine,
hydroxy,
straight or branched alkyl of from one to three carbon atoms, or
alkoxyl of from one to four carbon atoms;
$R_2$ is selected from
hydrogen;
straight or branched alkyl of from one to six carbon atoms unsubstituted or substituted with hydroxy or alkoxyl of from one to four carbon atoms;
straight or branched alkenyl of from one to six carbon atoms unsubstituted or substituted with hydroxy or alkoxyl of from one to four carbon atoms;
straight or branched alkynyl of from one to six carbon atoms unsubstituted or substituted with hydroxy or alkoxyl of from one to four carbon atoms;
cycloalkyl of from three to six carbon atoms;

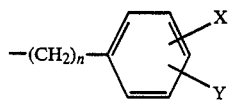

where n is zero to four and
X and Y are independently selected from
hydrogen,
fluorine,
chlorine,
bromine,
hydroxy,
straight or branched alkyl of from one to three carbon atoms, or alkoxyl of from one to four carbon atoms;

or a pharmaceutically acceptable acid addition salt thereof.

2. A method of treating pain in a mammal comprising administering an analgesically effective amount of a compound having the formula

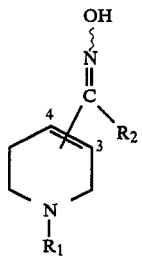

ps wherein
$R_1$ is
hydrogen;
straight or branched alkyl of from one to six carbon atoms unsubstituted or substituted with hydroxy or alkoxyl of from one to four carbon atoms;
straight or branched alkenyl of from one to six carbon atoms unsubstituted or substituted with hydroxy or alkoxyl of from one to four carbon atoms;
straight or branched alkynyl of from one to six carbon atoms unsubstituted or substituted with hydroxy or alkoxyl of from one to four carbon atoms;
cycloalkyl of from three to eight carbon atoms;

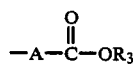

where A is a bond or is a hydrocarbon chain of from one to four carbon atoms, unsubstituted or substituted with halogen, and when containing two or more carbon atoms may contain one double bond and $R_3$ is alkyl of from one to six carbon atoms; or

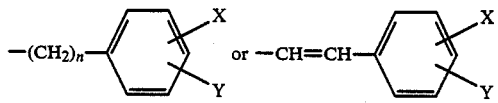

where n is zero to four and X and Y are independently selected from
hydrogen,
fluorine,
chlorine,
bromine,
hydroxy,
straight or branched alkyl of from one to three carbon atoms, or
alkoxyl of from one to four carbon atoms;
$R_2$ is selected from
hydrogen;
straight or branched alkyl of from one to six carbon atoms unsubstituted or substituted with hydroxy or alkoxyl of from one to four carbon atoms;
straight or branched alkenyl of from one to six carbon atoms unsubstituted or substituted with hydroxy or alkoxyl of from one to four carbon atoms;
straight or branched alkynyl of from one to six carbon atoms unsubstituted or substituted with hydroxy or alkoxyl of from one to four carbon atoms;
cycloalkyl of from three to six carbon atoms;

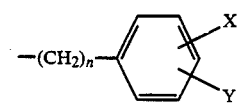

where n is zero to four and
X and Y are independently selected from
hydrogen,
fluorine,
chlorine,
bromine,
hydroxy,
straight or branched alkyl of from one to three carbon atoms, or alkoxyl of from one to four carbon atoms;

or a pharmaceutically acceptable acid addition salt thereof.

3. A method in accordance with claim 1 wherein said compound is 1-(1,2,5,6-tetrahydro-1-methyl-3-pyridinyl)ethanone oxime or a pharmaceutically acceptable salt thereof.

4. A method in accordance with claim 2 wherein said compound is 1-(1,2,5,6-tetrahydro-1-methyl-3-pyridinyl)ethanone oxime or a pharmaceutically acceptable salt thereof.

5. A method as defined by claim 1 or claim 2 wherein said compound is 1,2,5,6-tetrahydro-1-methyl-3-pyridine-carboxaldehyde oxime.

6. A method as defined by claim 1 or claim 2 wherein said compound is 3-phenyl-1-(1,2,5,6-tetrahydro-1-methyl-3-pyridinyl)-1-propanone oxime.

7. A method as defined in claim 1 or claim 2 wherein said compound is 1-(1,2,5,6-tetrahydro-1-methyl-3-pyridinyl)-4-pentyn-1-one oxime.

8. A method as defined by claim 1 or claim 2 wherein said compound is phenyl(1,2,5,6-tetrahydro-1-methyl-3-pyridinyl)methanone oxime.

9. A method as defined by claim 1 or claim 2 wherein said compound is 3-phenyl-1-(1,2,5,6-tetrahydro-1-propyl-3-pyridinyl)-1-propanone oxime.

10. A method as defined by claim 1 or claim 2 wherein said compound is 1-(1,2,5,6-tetrahydro-3pyridinyl)ethanone oxime.

11. A method as defined by claim 1 or claim 2 wherein said compound is 1-(1,2,5,6-tetrahydro-1-methyl-3-pyridinyl)-4-hexyn-1-one oxime.

12. A method as defined by claim 1 or claim 2 wherein said compound is 1-(1,2,5,6-tetrahydro-4-pyridinyl)ethanone oxime.

* * * * *